United States Patent [19]

Debat

[11] 4,186,211

[45] Jan. 29, 1980

[54] HIGHER ALKANOL COMPOSITIONS AND THE USE THEREOF IN TREATMENT OF PROSTATE DISORDERS

[75] Inventor: Jacques Debat, Paris, France

[73] Assignee: Societe Dite: Institut de Recherches Chimiques et Biologiques Appliquees-I.R.C.E.B.A., Paris, France

[21] Appl. No.: 502,036

[22] Filed: Aug. 30, 1974

[30] Foreign Application Priority Data

Aug. 29, 1974 [GB] United Kingdom ............... 40568/74

[51] Int. Cl.$^2$ .......................................... A61K 31/045
[52] U.S. Cl. ................................................ 424/343
[58] Field of Search .......................................... 424/343

[56] References Cited

U.S. PATENT DOCUMENTS

| | | | |
|---|---|---|---|
| 3,031,376 | 4/1962 | Levin et al. | 424/343 |
| 3,226,295 | 12/1965 | Goetz et al. | 424/343 |
| 3,646,215 | 2/1972 | Philips | 424/343 |
| 3,929,869 | 12/1975 | Guyod et al. | 424/343 |

OTHER PUBLICATIONS

Farm. Aikak. 79(11) 191–202 (1970)–Juslin et al.
Farm. Aikak. 80(5) 197–209 (1971)–Juslin et al.
Farm. Aikak. 80(6) 255–262 (1971)–Juslin et al.
Chem. Abst. 72,103760(p) (1970)–Katz et al.
Chem. Abst. 74,130338(e) (1971)–Juslin et al.
Chem. Abst. 75,121,359(f) (71)–Juslin et al.

*Primary Examiner*—Douglas W. Robinson
*Attorney, Agent, or Firm*—Bucknam and Archer

[57] ABSTRACT

This invention is concerned with a therapeutic composition intended in particular for the treatment of secretory disorders of the prostate gland, containing a pharmaceutically active quantity of at least one higher alkanol with 16 or more carbon atoms or one of its esters in association with a physiologically acceptable vehicle.

11 Claims, No Drawings

HIGHER ALKANOL COMPOSITIONS AND THE USE THEREOF IN TREATMENT OF PROSTATE DISORDERS

This invention relates to the therapeutic application of higher alkanols as active ingredients in the treatment of secretory disorders of the prostate gland and, more especially, in the treatment of prostatic adenoma.

It has surprisingly been found that it is possible successfully to treat patients suffering from secretory disorders of the prostate gland with a medicament containing at least one higher alkanol or one of its esters as active ingredient.

Accordingly, the invention relates to a therapeutic composition intended in particular for the treatment of secretory disorders of the prostate gland, such as prostatic adenoma, distinguished by the fact that it contains a therapeutically active quantity of at least one higher alkanol or one of its esters in association with a physiologically acceptable excipient.

In the context of the invention, higher alkanols are primary and secondary alcohols containing at least 16 carbon atoms and corresponding to the general formula

in which $R_1$ represents a linear or branched, saturated or unsaturated hydrocarbon radical, $R_2$ represents the hydrogen atom or a linear or branched saturated or unsaturated hydrocarbon radical, the number of carbon atoms present in $R_1$ and $R_2$ together being greater than or equal to 15.

The alkanols of formula I containing 16 or more carbon atoms can be prepared by a method known per se, for example by reducing the corresponding acid or by reducing the corresponding carbonyl derivative (aldehyde or ketone). In general, the optionally saturated higher alkanols of formula I can be prepared by the methods described in Traite de Chimie Organique by Victor GRIGNARD, Volume V, pages 615 to 641, published by MASSON & Gie, Paris 1937.

Examples of suitable methods of preparation are given in the following to illustrate the invention.

EXAMPLE 1: 1-docosanol

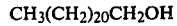

Principle of preparation

Reduction of the corresponding acid with LiAlH$_4$ in ether, followed by hydrolysis with a dilute acid in aqueous solution.

Method:

4 g of docosanoic acid are dissolved in 150 ml of anhydrous ether. LeAlH$_4$ is progressively introduced. On completion of the reaction, 150 ml of an aqueous solution of 1 N acetic acid are introduced. The ethereal phase is then separated off, decanted and dried. Rectification in vacuo gives approximately 1 g of 1-docosanol.
Melting point: 69°-71° C.
Boiling point: 180° C. at 0.22 mm Hg
Microanalysis found for $C_{22}H_{46}O$: C%=80.98 H%=14.11 O%=4.90.

The alkanols of Examples 2 to 6 were obtained by reducing the corresponding acid or carbonyl derivative.

EXAMPLE 2: 13cis-docosen-1-ol

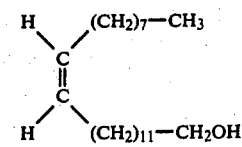

Analysis for $C_{22}H_{44}O$:
Calculated: C=81.40%; H=13.55%
Found: C=81.20%; H=13.60%.

EXAMPLE 3: 9cis, 12cis-octadecadien-1-ol

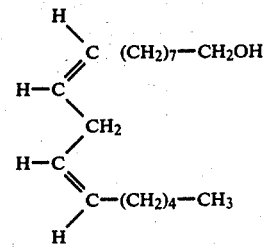

Analysis for $C_{18}H_{34}O$:
Calculated: C=81.12%; H=12.76%
Found: C=80.20%; H=12.90%.

EXAMPLE 4: (limited Example)

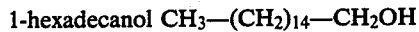

Melting point (test tube): 49°-50° C.
Boiling point: 130°-132° C. at 1 mm Hg
Analysis for $C_{16}H_{34}O$: Calculated: C=79.34%; H=14.04% Found: C=79.80%; H=13.90%

EXAMPLE 5: (comparative Example)

Melting point (test tube): 25°-26° C.
Boiling point: 100°-101° C. at 1 mm Hg
Analysis for $C_{12}H_{26}O$:
Calculated: C=77.42%; H=13.98%
Found: C=77.60%; H=13.80%.

EXAMPLE 6: 2-eicosanol

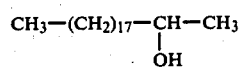

Melting point: 60°-61° C.
The product of Example 6 was also obtained by a more practical method described below.

EXAMPLE 6bis: 2-eicosanol 72.3 g of 1-chloroctadecane ($C_{18}H_{37}Cl$) are dissolved in 200 ml of anhydrous diethyl ether, followed by the introduction of 6.1 g of thoroughly dried magnesium turnings. 11 g of acetaldehyde dissolved in 50 ml of anhydrous diethyl ether are then progressively added. The mixture is cooled under a stream of cold water and stirred for 3 hours.

The organometallic compound thus obtained is then decomposed by stirring with 75 ml of a saturated solution of ammonium chloride. The ethereal phase is separated off, washed with water, dried over anhydrous $Na_2SO_4$ and then evaporated. The product obtained, which is 2-eicosanol, is recrystallised from petroleum ether.

Melting point: 60°–61° C.

Analysis for $C_{20}H_{42}O$:

Calculated: C=80.53%; H=14.09%

Found: C=80.70%; H=14.01%.

Liquid or solid, physiologically acceptable vehicles can be used for preparing therapeutic compositions containing the higher alkanols according to the invention. Solid preparations include in particular powders, tablets, granules, capsules, dragees, gelatin-coated pills and suppositories.

The solid vehicle which can be used contains one or more substances acting as diluent, solubilising perfume, lubricant, binder, surfactant or disintegrating agent (in the case of tablets). The solid vehicle can also contain one or more encapsulating substances.

In powder form, the active compound is associated with the solid vehicle in finely divided form. In tablets, the active compound is mixed in suitable proportions with a vehicle having the required binding properties. Powders and tablets contain from 1 to 90% by weight of active ingredient. Suitable solid vehicles include in particular magnesium carbonate, magnesium stearate, talcum, saccharose, glucose, lactose, pectin, dextrin, starch, gelatin, tragacanth, methyl cellulose, sodium carboxymethyl cellulose, waxes of low melting point and cocoa butter.

Liquid preparations include solutions, suspensions and emulsions. In this case, the vehicle can consist on the one hand of an aqueous solution of polyethylene glycol or polypropylene glycol and, on the other hand, of oil, especially olive oil.

Aqueous suspensions for oral administration are prepared by dispersing the finely divided active compound in water with a viscous substance, a natural or synthetic gum, a resin or the like, for example with gum arabic, an ion-exchange resin, methyl cellulose, carboxymethyl cellulose or any other well-known suspending agent.

The results of pharmacological tests which have been conducted are summarised in the following.

Histological modifications to the epithelium of adult rats were examined. It was found that the compounds according to the invention were capable of stimulating the function of the prostate gland in adult rats treated orally for 15 days to 3 months with very small doses, because a considerable improvement was observed, for example, in the case of the product of Example 1 administered in a dose of 0.5 mg per kg of bodyweight per day.

TECHNIQUE

The higher alkanol is administered daily for the period indicated to adult rats aged about 9 months in the dose indicated in an excipient which is, for example, olive oil.

Control rats are only given the excipient.

In the experiment described, the animals were treated 6 days a week for 7 weeks. The higher alkanol was administered in solution in a volume of 0.1 ml per 100 g of bodyweight, i.e. in a concentration of 0.5 g of product per liter of oil.

At the end of the experiment, the control animals and treated animals were killed, the ventral section of their prostate glands removed, kept in an alcohol bath and then histologically examined.

The appearance of the prostate sections is assessed in accordance with the following scale:

Epithelium+1

Enlargement of the peripheral epithelium of the central glands assuming a cubic appearance and occupying more than the outer half of the surface of the prostate.

Epithelium+2

Enlargement of the epithelium which becomes cylindrical in appearance throughout.

Epithelium+3

Epithelium identical throughout with those of the peripheral glands.

Epithelium+4

Papillary hyperlesion of the epithelium with hypersecretion (this "step" was not observed in the tests carried out).

The results relating to the ventral prostates examined after killing of the control animals and of the animals treated with 1-docosanol in the dose indicated are given in Tables I and II below:

TABLE I

| Groups | Number of animals | Central examination of organ | | |
|---|---|---|---|---|
| | | Epithelium 1+ | Epithelium 2+ | Epithelium 3+ |
| Controls | 19 | 14 | 5 | 0 |
| Treated | 20 | 4 | 16 | 0 |

TABLE II

| Groups | Number of animals | Peripheral examination | | |
|---|---|---|---|---|
| | | Epithelium 1+ | Epithelium 2+ | Epithelium 3+ |
| Controls | 19 | 5 | 10 | 4 |
| Treated | 20 | 0 | 13 | 7 |

Statistical calculations

Table I shows that the animals divide into two groups according to the condition of their epithelium. The control group and the treated group were compared by the method known as Chi 2 which, in this example has the value 11.167 which, with one degree of freedom, gives a significant difference probability of greater than 999/1 000 for the effectiveness of 1-docosanol.

In Table II, the animals are divided into three groups according to the condition of their prostatic epithelium. The Chi 2 assumes the value 6.360 which, with two degrees of freedom, gives a significant difference probability of 95 and 98/100 for the effectiveness of 1-docosanol.

The results of the tests carried out with the products of Examples 2 to 6 by the technique specified above are set out in Table III below.

TABLE III

| Groups | Number of animals | Examination of the periphery of the prostate | | |
|---|---|---|---|---|
| | | Epithelium 1+ | Epithelium 2+ | Epithelium 3+ |
| Controls | 30 | 11 | 14 | 5 |

TABLE III-continued

| | Examination of the periphery of the prostate | | | |
|---|---|---|---|---|
| Groups | Number of animals | Epithelium 1+ | Epithelium 2+ | Epithelium 3+ |
| Example 2 | 15 | 2 | 7 | 6 |
| Example 3 | 15 | 3 | 4 | 8 |
| Example 4 | 16 | 4 | 8 | 4 |
| Example 5 | 15 | 5 | 8 | 2 |
| Example 6 | 15 | 3 | 4 | 8 |

Statistical analysis of the results set out in Table III shows (a) that the products of Example 2, 3, and 6 are significantly active, (b) that the product of Example 5 is significantly inactive (results identical with the controls) and (c) that the product of Example 4 is substantially inactive.

It is apparent from the tests described above that, among the series of alkanols, alcohols containing less than 16 carbon atoms are inactive, whilst alcohols containing more than 16 carbon atoms are active, the limit being at 16 carbon atoms, as illustrated in Example 4.

In other words, if the EPP index (examination of the periphery of the prostate) is defined as the ratio of the sum of all the subjects classified as "epithelium 1+" with the coefficient 1, as "epithelium 2+" with the coefficient 2 and as "epithelium 3+" with the coefficient 3, to the number of animals, it is found as indicated in Table IV below that inactivity prevails where EEP is less than 2, whilst activity at prostate level prevails where EEP is greater than 2.

TABLE IV

| Groups | EPP* |
|---|---|
| Controls (Table II) | 37:19 = 1.94 |
| Controls (Table III) | 54:30 = 1.80 |
| Example 1 | 47:20 = 2.35 |
| Example 2 | 34:15 = 2.26 |
| Example 3 | 35:15 = 2.33 |
| Example 6 | 35:15 = 2.33 |
| Example 4 | 32:16 = 2.00 |
| Example 5 | 27:15 = 1.80 |

*$EPP = \dfrac{1 \times (\text{epithelium } 1+) + 2 \times (\text{epithelium } 2+) + 3 \times (\text{epithelium } 3+)}{\text{number of animals examined}}$ It is apparent from the foregoing that higher alkanols containing 16 or more carbon atoms, more especially 1-docosanol which is the preferred product, act positively on the prostate gland by restoring its function to normal in the case of secretory disorders attributable to deficiency of this organ.

I claim:

1. The method of treatment of enlargement of the prostate gland which comprises administering to a patient in need of said treatment a composition containing a therapeutically effective amount of 1-docosanol, 13-cis-docosen-1-ol, 9-cis, 12-cis-octadecadien-1-ol, or 2-eicosanol in association with a physiologically acceptable vehicle.

2. The method of treatment of enlargement of the prostate gland which comprises administering to a patient in need of said treatment of composition containing a therapeutically effective amount of 1-docosanol in association with a physiologically acceptable vehicle.

3. The method of treatment of enlargement of the prostate gland which comprises administering to a patient in need of said treatment a composition containing a therapeutically effective amount of 13-cis-docosen-1-ol in association with a physiologically acceptable vehicle.

4. The method of treatment of enlargement of the prostate gland which comprises administering to a patient in need of said treatment a composition containing a therapeutically effective amount of 9-cis, 12-cis-octadecadien-1-ol in association with a physiologically acceptable vehicle.

5. The method of treatment of enlargement of the prostate gland which comprises administering to a patient in need of said treatment a composition containing a therapeutically effective amount of 2-eicosanol in association with a physiologically acceptable vehicle.

6. The method according to claim 2 wherein the amount of 1-docosanol is 0.5 mg. per kg. of body weight per day.

7. A pharmaceutical composition for the treatment of the enlargement of the prostate gland containing as the only active ingredient 1-docosanol, 13-cis-docosen-1-ol, 9-cis, 12-cis-octadecadien-1-ol or 2-eicosanol in the amount of 1-90% by weight of the composition in association with a physiologically acceptable vehicle, which is selected from the group consisting of magnesium carbonate, magnesium stearate, talcum, saccharose, glucose, lactose, pectin, dextrin, starch, gelatin, tragacanth, gum arabic, methyl cellulose, sodium carboxymethyl cellulose, a low melting wax, cocoa butter, polyethylene glycol, polypropylene glycol and olive oil.

8. A pharmaceutical composition containing as the sole active ingredient a therapeutically effective amount of 1-docosanol, in association with a physiologically acceptable vehicle, which is selected from the group consisting of magnesium carbonate, magnesium stearate talcum, saccharose, glucose, lactose, pectin, dextrin, starch, gelatin, tragacanth, gum arabic, methyl cellulose, sodium carobxymethyl cellulose, a low melting eas, cocoa butter, polyethylene glycol, polypropylene glycol and olive oil.

9. A pharmaceutical composition containing as the sole active ingredient a therapeutically effective amount of 13-cis-docosen-1-ol, in association with a physiologically acceptable vehicle, which is selected from the group consisting of magnesium carbonate, magnesium stearate, talcum, saccharose, glucose, lactose, pectin, dextrin, starch, gelatin, tragacanth, gum arabic, methyl cellulose, sodium carboxymethyl cellulose, a low melting wax, cocoa butter, polyethylene glycol, polypropylene glycol and olive oil.

10. A pharmaceutical composition containing as the sole active ingredient a therapeutically effective of amount of 9-cis, 12-cis-octadecadien-1-ol, in association with a physiologically acceptable vehicle, which is selected from the group consisting of magnesium carbonate, magnesium stearate, talcum, saccharose, glucose, lactose, pectin, dextrin, starch, gelatin, tragacanth, gum arabic, methyl cellulose, sodium carboxymethyl cellulose, a low melting wax, cocoa butter, polyethylene glycol, polypropylene glycol and olive oil.

11. A pharmaceutically composition containing as the sole active ingredient a therapeutical effective amount of 2-eicosanol, in association with a physiologically acceptable vehicle, which is selected from the group consisting of magnesium carbonate, magnesium stearate, talcum, saccharose, glucose, lactose, pectin, dextrin, starch, gelatin, tragacanth, gum arabic, methyl cellulose, sodium carboxymethyl cellulose, a low melting wax, cocoa butter, polyethylene glycol, polypropylene glycol and olive oil.

* * * * *

UNITED STATES PATENT AND TRADEMARK OFFICE
CERTIFICATE OF CORRECTION

PATENT NO. : 4,186,211
DATED : January 29, 1980
INVENTOR(S) : Jacques Debat

It is certified that error appears in the above—identified patent and that said Letters Patent is hereby corrected as shown below:

On the title page delete

"(30) Foreign Application Priority Data
Aug. 29, 1974 (GB) United Kingdom........40568/74"

*Signed and Sealed this*

*Twenty-sixth* Day of *May 1981*

[SEAL]

*Attest:*

RENE D. TEGTMEYER

*Attesting Officer*   *Acting Commissioner of Patents and Trademarks*